United States Patent [19]
Chiu

[11] Patent Number: 5,672,727
[45] Date of Patent: Sep. 30, 1997

[54] DITHIOCARBAMOYL DIOLS AND BORATE ESTERS THEREOF FOR USE IN LUBRICANT COMPOSITIONS

[75] Inventor: I-Ching Chiu, Houston, Tex.

[73] Assignee: Pennzoil Products Company, The Woodlands, Tex.

[21] Appl. No.: 667,174

[22] Filed: Jun. 20, 1996

Related U.S. Application Data

[62] Division of Ser. No. 851,265, Mar. 13, 1992, Pat. No. 5,560,853, which is a continuation of Ser. No. 574,714, Aug. 30, 1990, abandoned.

[51] Int. Cl.$^6$ .................. C07C 333/04; C07C 333/06; C07C 333/08
[52] U.S. Cl. .................................................. 558/236
[58] Field of Search .......................................... 558/236

[56] References Cited

U.S. PATENT DOCUMENTS

| | | |
|---|---|---|
| 2,394,536 | 2/1946 | Denison et al. . |
| 2,467,916 | 8/1949 | Kaiser . |
| 2,649,473 | 8/1953 | Chenuck . |
| 2,691,632 | 10/1954 | Harle . |
| 2,928,812 | 3/1960 | Ernst . |
| 2,975,134 | 3/1961 | Cook . |
| 2,998,445 | 8/1961 | Stewart . |
| 3,081,335 | 3/1963 | Morris et al. . |
| 3,282,978 | 11/1966 | Swakon . |
| 3,338,832 | 8/1967 | LeSuer . |
| 3,558,685 | 1/1971 | Osieka et al. . |
| 3,867,359 | 2/1975 | Beadle ................... 525/352 |
| 4,115,286 | 9/1978 | Baldwin et al. . |
| 4,225,450 | 9/1980 | Rosenberger . |
| 4,271,167 | 6/1981 | Bourzat et al. ............. 514/352 |
| 4,399,044 | 8/1983 | Richmond . |
| 4,692,257 | 9/1987 | Horodysky . |
| 4,859,353 | 8/1989 | Colclough . |
| 4,997,969 | 3/1991 | Luciani . |

OTHER PUBLICATIONS

Database CAPLUS on STN, Accession No. 1971: 63952, Columbus:Chemical Abstracts Service; Konecny, V., CS 134162, published Nov. 15, 1969.

Database CAPLUS on STN, Accession No. 1991: 82424, Columbus: Chemical Abstracts Service; Postel, D.G. et al., FR 2638457, published May 4, 1990.

Primary Examiner—Johann Richter
Assistant Examiner—Michael G. Ambrose
Attorney, Agent, or Firm—Lowe, Price, LeBlanc & Becker

[57] ABSTRACT

An alkyl dithiocarbamoyl alkanol that has the formula

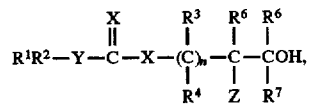

wherein

Z is H or OH, Y is N, X is S, $R^1$ and $R^2$ are, selected from the group consisting of H and ($C_1$-$C_{40}$)hydrocarbon residues $R^3$, $R^4$, $R^5$, $R^6$ and $R^7$ are selected from the group consisting of H and ($C_1$-$C_8$)hydrocarbon residues, n is 0 to 4, is an intermediate to prepare a borate ester having the formula

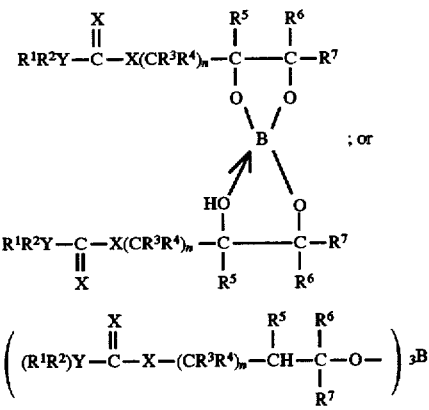

The borate esters are anti-wear/anti-oxidant/anti-friction/anti-rust additives for lubricating oil.

8 Claims, No Drawings

DITHIOCARBAMOYL DIOLS AND BORATE ESTERS THEREOF FOR USE IN LUBRICANT COMPOSITIONS

This application is a division of application Ser. No. 07/851,265 filed Mar. 13, 1992, now U.S. Pat. No. 5,560,835, which is a continuation of Ser. No. 07/574,714, filed Aug. 30, 1990, now abandoned.

TECHNICAL FIELD

This invention relates to dithiocarbamoyl alkanols as intermediates and to borate esters of the dithiocarbamoyl alkanols which are useful as anti-wear/anti-oxidant/anti-friction/anti-rust multifunctional additives. This invention also relates to anti-wear/anti-oxidant/anti-friction/anti-rust compositions comprising a lubricant and the anti-wear/anti-oxidant/anti-friction/anti-rust multifunctional additives of the invention. The borate esters of the invention are useful as lubricant additives to, e.g., replace or reduce the zinc dialkyldithiophosphate (ZDDP) needed in engines.

BACKGROUND ART

Various zinc dialkyldithiophosphates (ZDDP) are known as very effective anti-wear, anti-oxidant additives. These compounds have been used as additives for lubricating oils since the early 1940s. However, due to their phosphorus contents, the addition of ZDDPs to motor oils adversely affects the catalytic efficiency of exhaust emission catalytic converters which are installed nowadays in most cars to reduce pollutants in the exhaust gas. In addition, metallic ZDDPs can cause ash formation and have antagonistic interactions with dispersants which are normally added to lubricants. Thus, non-metallic, ashless anti-wear/anti-oxidant products which can replace ZDDPs as additives to lubricants will have a lesser tendency to produce sludge.

A number of dithiocarbamate derivatives have been known to be useful as lubricant additives (e.g., U.S. Pat. Nos. 3,890,363; 3,833,496; 4,440,676; 4,502,972; 4,795,684; 4,758,362; 4,125,479; 3,856,836; 3,342,835; 4,400,298; 3,462,368; 3,412,026; EP Patent No. 211,806; EP Patent No. 285,455; EP Patent No. 220,136; and W.O. Patent No. 87/05622).

A significant number of borate esters of mono- and di-hydroxy derivatives have also been known as has their use as lubricant additives (e.g., U.S. Pat. Nos. 4,486,323; 4,486,321; 4,273,665; 4,374,032; 4,376,712; 4,382,006; 4,328,113; 4,410,436; 4,447,560; 4,507,216; 4,400,284; 4,440,656; EP Patent No. 36,708; EP Patent No. 285,455; EP Patent No. 220,136; and German Offen. No. 3,327,859).

Therefore, due to environmental concerns, there is a need for specially formulated lubricants which contain no phosphorus or only a very low concentration of phosphorus.

DISCLOSURE OF THE INVENTION

This invention relates to an alkyl dithiocarbamoyl alkanol of the formula

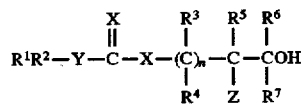

wherein
Z is OH or H;
Y is N
X is S;

$R^1$ and $R^2$ are independent of one another, selected from the group consisting of H, $(C_1-C_{40})$hydrocarbon residues and $(C_3-C_{50})$cycloalkyl, aryl, and aralkyl, each of which may further contain N, O or S;

$R^3$, $R^4$, $R^5$, $R^6$ and $R^7$ are independent of one another and are selected from the group consisting of H and $(C_1-C_8)$hydrocarbon residues; and n is 0 to 4.

The alkanols of formula (I) are useful as intermediates for preparation of the borate esters of this invention as described below. When Z is OH in Formula I the borate esters of Formula (II) are produced therefrom. When Z is H, the borate esters of Formula (III) are produced therefrom.

This invention also relates to borate esters selected from those of the formulae:

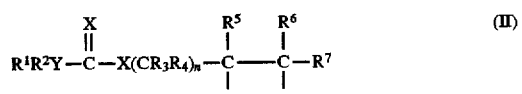

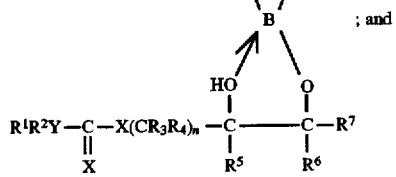

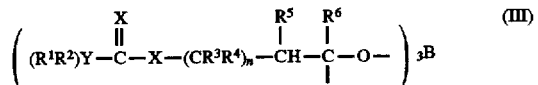

wherein
Y is N;
X is S;
$R^1$ and $R^2$ are independent of one another, selected from the group consisting of H, $(C_1-C_{40})$hydrocarbon residues and $(C_3-C_{50})$cycloalkyl, aryl and aralkyl, each of which may further contain N, O or S;

$R^3$, $R^4$ $R^5$, $R^6$ and $R^7$ are independent of one another selected from the group consisting of H and $(C_1-C_8)$ hydrocarbon residues; and n is 0 to 4.

Also part of this invention are anti-wear/anti-oxidant/anti-friction/anti-rust additives which comprise an anti-wear/anti-oxidant/anti-friction/anti-rust amount of a borate ester of this invention. The borate esters of this invention are multifunctional, that is, they provide one or more properties to lubricating oil such as anti-wear, anti-friction and/or anti-rust characteristics.

Also encompassed by this invention is an anti-wear/anti-oxidant/anti-friction/anti-rust composition, which comprises
a lubricant; and
an effective amount of an anti-wear/anti-oxidant/anti-friction/anti-rust additive of this invention.

Provided herein is also a method of reducing wear, oxidation, friction and/or rust in an engine which comprises adding to the engine the anti-wear/anti-oxidant/anti-friction/anti-rust composition of this invention described above.

A more complete appreciation of the invention and many of the attendant advantages thereof will be readily perceived as the same becomes better understood by reference to the following detailed description. Other objects, advantages and features of the present invention will become apparent to those skilled in the art from the following discussion.

BEST MODE FOR CARRYING OUT THE INVENTION

The intermediate alkyl dithiocarbamoyl alkanols of the invention have the formula

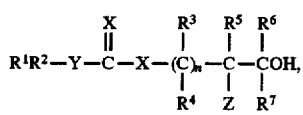

(I)

wherein z is OH or H;

Y is N;

X is S;

R$^1$ and R$^2$ are independent of one another, selected from the group consisting of H, (C$_1$–C$_{40}$)hydrocarbon residues and (C$_3$–C$_{50}$)cycloalkyl, aryl and aralkyl each of which may further contain N, O or S;

R$^3$, R$^4$, R$^5$, R$^6$ and R$^7$ are, independent of one another, selected from the group consisting of H and (C$_1$–C$_8$)-hydrocarbon residues; and n is 0 to 4.

In a preferred embodiment n is 1 to 3. In other preferred embodiments, Y is N, and X is S. Still other preferred embodiments are those where R$^1$ and R$^2$, independent of one another, are (C$_3$ to C$_{20}$)hydrocarbon residues, which may be either straight or branched chain hydrocarbon residues. Other preferred embodiments are those where R$^1$ and/or R$^2$ are (C$_3$–C$_{20}$)hydrocarbon residues comprising one or more of N, O and S atoms in the hydrocarbon chain. Other preferred embodiments are those where R$^3$, R$^4$, R$^5$, R$^6$ and R$^7$ independent of one another are (C$_1$–C$_8$)hydrocarbon residues or hydrogen. A most preferred group of alkyl dithiocarbamoyl alkanols are 3-bis(2-ethylhexyl) dithiocarbamoyl-1,2-propanediol; 3-dioctyl-dithiocarbamoyl-1,2-propanediol; 2-bis(2-ethylhexyl) dithiocarbamoyl-ethanol; and 3-oleyl-dithiocarbamoyl-1,2-propanediol.

The above compounds of Formula (I) of this invention may be prepared by the reaction of, e.g., a secondary or primary amine with, e.g., carbon disulfide to form the corresponding dithiocarbamic acid. The product is then reacted with about stoichiometric amounts of 3-chloro-1,2-propanediol, or glycidol, to give a dihydroxy derivative as a product. Alternatively, the product may then be reacted with a stoichiometric amount of 2-chloroethanol or ethylene oxide to give a monohydroxy derivative as a product as depicted in the following scheme.

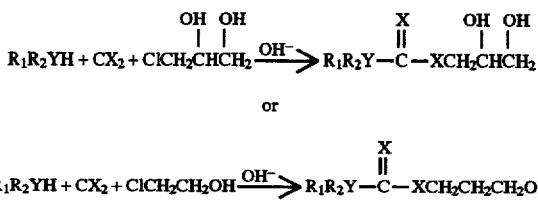

The structure of the compounds of the invention were confirmed by C-13 NMR, infrared spectra and boron analysis (by atomic absorption) as is known in the art.

Suitable amines for preparing the above compounds are R$^1$R$^2$NH, wherein R$^1$ and R$^2$ are as previously defined. The symmetric secondary amines include dimethylamine, diethylamine, dipropylamine, dibutylamine, diamylamine, dihexylamine, dioctylamine, diheptylamine, bis(2-ethylhexyl)amine, dicocoamine, and di(hydrogenated tallow)amine, and the like. The non-symmetric secondary amines include N-methyl-N-ethylamine, N-ethyl-N-butylamine, N-ethyl-N-amylamine, N-methyl-N-octadecylamine, and the like. The primary amines include methylamine, ethylamine, propylamine, butylamine, pentylamine, hexylamine, heptylamine, octylamine, decylamine, undecylamine, dodecylamine, tetradecylamine, hexadecylamine, octadecylamine, oleylamine, soyaamine, tallowamine, N-tallow-1,3-propanediamine, N-soya-1,3-propanediamine, N-coco-1,3-propanediamine, N-oleyl-1,3-propanediamine and the like.

Suitable hydroxylalkylating agents are, among others,

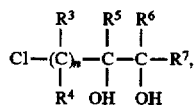

wherein

R$^3$, R$^4$, R$^5$, R$^6$ and R$^7$ are independent of one another, hydrogen or (C$_1$–C$_8$)hydrocarbon residues;

n is 0–4.

Representative compounds are 3-chloro-1,2-propanediol, 2-chloroethanol, 3-chloro-1-propanol, 4-chloro-1-butanol. Heteroatom-containing (CR$^3$R$^4$)$_n$ radicals, such as 2-(2-chloroethoxy)ethanol, among others, are also suitable.

Alternative hydroxyalkylating agents are oxirane derivatives such as glycidol, ethylene oxide, propylene oxide and the like. 3-Chloro-1,2-propanediol, for instance, can be prepared by reacting glycerol and hydrochloric acid. For reasons of economy, epichlorohydrin, which undergoes acid catalytic hydrolysis in water to give 3-chloro-1,2-propanediol, is preferred for the preparation of the compounds of this invention. The acid catalyst can be selected from inorganic acids such as sulfuric acid, perchloric acid and nitric acid and organic acids such as acetic acid.

The hydroxyalkylation reaction can be carried out with or without a solvent. If oxirane derivatives are used as an hydroxyalkylating agent, the reactions are preferably carried out without solvent. On the other hand, if chlorinated compounds are used as hydroxyalkylation agents, the reactions are carried out with solvents selected from water and hydrocarbon solvents.

A stiochiometric amount of base may also be added. The base can be inorganic or organic. Inorganic bases include sodium hydroxide, potassium hydroxide, sodium hydride, potassium hydride, and the like. Organic bases include an amine such as triethylamine, and the like. The reaction temperature can vary from about 0° C. to 100° C., and preferably is room temperature.

Also provided herein is a borate ester selected from those of the formula

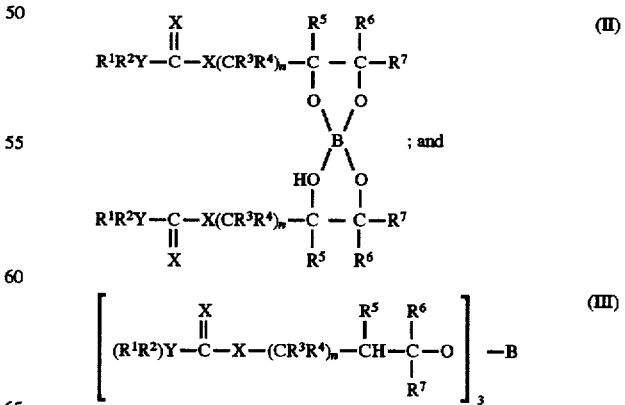

wherein

Y is N;

X is or S;

$R^1$ and $R^2$ are, independent of one another, selected from the group consisting of H, ($C_1$–$C_{40}$)hydrocarbon residues and ($C_3$–$C_{50}$)cycloalkyl, aryl and aralkyl, each of which may further contain N, O or S;

$R^3$, $R^4$, $R^5$, $R^6$ and $R^7$ are, independent of one another, selected from the group consisting of H and ($C_1$–$C_8$)-hydrocarbon residues; and n is 0 to 4.

Preferred embodiments are those where the borate ester has the formula

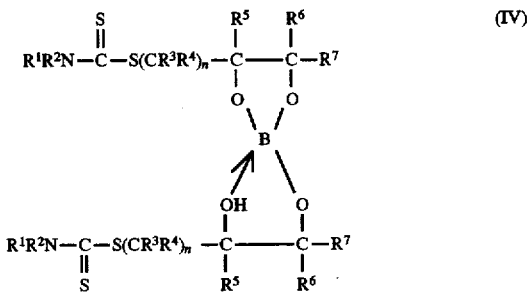

Another preferred embodiment of the invention is where the borate ester has the formula

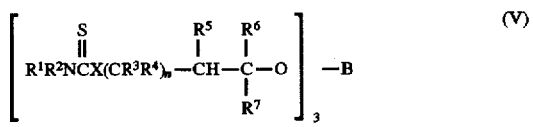

The borate esters of the invention may be prepared by reacting a borating agent, e.g., boric acid, with the compounds of Formula I described above as depicted in the following scheme.

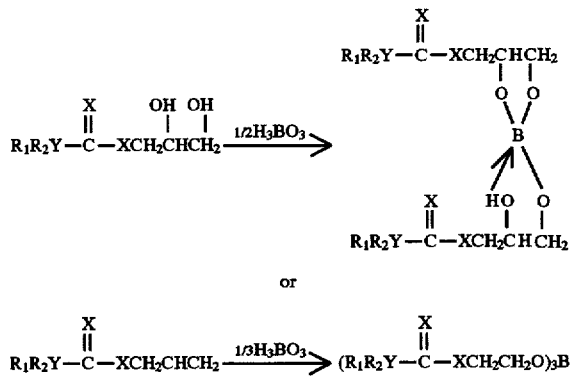

The borating reaction may also be conducted with other borating agents. Suitable borating agents in this invention include boric acid, boron oxide, trialkyl borates and borate esters derived from hindered phenolic anti-oxidants as described in, e.g., U.S. Pat. Nos. 4,162,224 and 4,507,216.

The water obtained as a reaction by-product of the borating reaction may be stripped off under reduced pressured if the reaction is run without a solvent. If the reaction is carried out with a solvent, which may include benzene, toluene, and xylene, among others, the water may be trapped in a Dean-Stark trap at reflux temperature.

To increase the anti-oxidant properties, the metal salts of the borate complexes may be obtained by reaction of the esters with a salt of the metal. The above borate esters which are complexed with metal cations exhibit increased anti-oxidant properties when compared with the remaining borate esters of this invention.

Also provided herein is an anti-wear/anti-oxidant/anti-friction/anti-rust multifunctional additive which comprises an anti-wear/anti-oxidant/anti-friction and/or anti-rust amount of a borate ester of the invention described above. Typically, the additive may comprise about 0.001 to 99.99 wt % borate ester or metal salt thereof, and more preferably about 20 to 85 wt %, based on the amount of lubricating oil to which it is added.

Also provided herein is an anti-wear/anti-oxidant/anti-friction/anti-rust composition intended for use in engines, which comprises a lubricant; and an effective amount of an anti-wear/anti-oxidant/anti-friction and/or anti-rust multifunctional additive of this invention. By "effective amount" is meant that the borate ester is present in sufficient amounts to provide anti-wear, anti-oxidant, anti-friction and/or anti-rust properties to the lubricating oil.

The anti-wear/anti-oxidant/anti-friction/anti-rust composition preferably comprises about 0.5 to 5.0 wt % of the multifunctional additive, and more preferably about 0.75 to 1.75 wt %, based on the weight of lubricating oil. A most preferred composition is that wherein the additive is present in amount of about 1.0 wt %.

The compositions described above are prepared and compounded as is known in the art and packaged in unit form or in layer volumes for greater ease of transportation.

In a preferred embodiment of the invention the lubricant to which the additive is added may suitably be a lubricant oil such as mineral oil, a synthetic oil, or mixtures thereof. In addition, in another preferred embodiment, the lubricant may also be a grease or a liquid fuel. Suitable examples are known in the art. These anti-wear/anti-oxidant/anti-friction/anti-rust compositions are used in engines as is known in the art.

Also provided herein is a method of reducing wear, oxidation, friction and/or rust in an engine comprising adding to the engine the anti-wear/anti-oxidant/anti-friction/anti-rust composition of the invention described above. The composition of the invention suitably comprises amounts of the anti-wear/anti-oxidant/anti-friction/anti-rust additive as described hereinabove. Preferred amounts are about 0.5 to 5.0 wt % of the additive, and more preferably about 0.75 to 1.75 wt %, based on the weight of the oil.

Having now generally described this invention, the same will be better understood by reference to certain specific examples, which are included herein for purposes of illustration only and are not intended to be limiting of the invention or any embodiment thereof, unless so specified.

EXAMPLES

Example I

Preparation of 3-Bis(2-ethylhexyl)dithiocarbamoyl-1,2-propanediol (a) Method A

A 500 ml, 2-necked round-bottomed flask containing a magnetic stirring bar, equipped with an addition funnel and a thermometer was charged with bis(2-ethylhexyl)amine (169.05 grams). $CS_2$ (46.2 ml) was added dropwise. After the addition was completed, the reaction was stirred for one hour. Glycidol (51.8 grams) was then slowly added into the reaction flask. Since the reaction is exothermic, the reaction flask may need to be cooled in an ice bath occasionally.

After stirring for another hour at ambient temperature, the reaction, without any workup or further purification, yielded a yellow viscous liquid of the title compound (273.9 gram) in high purity as proven by thin-layer chromatograph and C-13 NMR spectrum.

(b) Method B

Carbon disulfide (33 ml) was slowly added into the stirred bis(2-ethylhexyl)amine (120.8 grams) at ambient temperature. After the reaction was stirred for one hour, 3-chloro-1,2-propanediol (55.27 grams) was added, followed by the slow addition of 2.5M aqueous NaOH (200 ml). After stirring for two hours, the reaction was repeatedly extracted with toluene.

After drying over $MgSO_4$ and filtering, the toluene extracts were concentrated under reduced pressure to yield 189.6 grams (97% yield) of the title compound as a yellow viscous liquid. Without stripping off the solvent, the extracts can be further treated with boric acid as described in Example II below.

(c) Method C

The same procedure of Method B was followed, except that 3-chloro-1,2-propanediol was prepared in situ from epichlorohydrin as follows. Epichlorohydrin (46.25 grams) was suspended in 1M aqueous $HClO_4$ (50 ml). The suspension was stirred at room temperature until the solution turned clear (about 1.5 hours). The clear aqueous solution was further heated at 50° C. for another half hour.

After cooling to room temperature, the aqueous solution was allowed to react with the aqueous solution of sodium bis(2-ethylhexyl)dithiocarbamate derived from bis(2-ethylhexyl)amine (120.8 grams), $CS_2$, (33 ml) and 2M aqueous NaOH (12.5 ml). The product, having an identical C-13 NMR spectrum as that of product prepared in Method A, was obtained in a 95% yield (185.7 grams).

Example II

Preparation of Borate Ester of 3-Bis(2-ethylhexyl)-1,2-propanediol

Boric acid (10.85 grams) was added to the 3-bis(2-ethylhexyl)dithiocarbamoyl-1,2-propanediol in toluene (100 ml) solution. The suspended solution was gradually heated to reflux. A Dean-Stark trap was used to collect the water of reaction. The reaction was refluxed for two hours until all the solid was consumed.

The solution was then filtered and the filtrate was concentrated under reduced pressure to give 138.94 g of yellow viscous liquid. Atomic absorption analysis gave B, 1.40 wt % (calculated value of boron for a dimeric structure is 1.36%). The C-13 NMR and IR spectra were all consistent with a dimeric structure as given in the embodiment.

Example III

Preparation of Borate Ester of 3-Bis(2-ethylhexyl)-1,2-propanediol Complex With 20% Equivalent of Copper Copper acetate monohydrate (0.80 grams) was added to a toluene (40 ml) solution of the borate ester of 3-bis(2-ethylhexyl)-1,2-propanediol (15.80 g, 20 mmol). The suspensed solution was gradually heated to reflux and kept at reflux until all the copper salt disappeared (about 3 hours). The reaction by-products, water and acetic acid, were trapped in a Dean-Stark trap. The reaction solution was filtered and the solvent was stripped off under reduced pressure.

A black viscous liquid of the title compound (16.27 grams) was obtained. The X-ray analysis showed the product contains 1.60 wt % of copper.

Example IV

Preparation of Borate Ester of 3-Dioctyldithiocarbamoyl-1,2-propanediol

The same procedure as Method A of Example I was followed, except that dioctylamine (48.3 grams) was allowed to react with glycidol (14.8 grams) and $CS_2$ (12.6 ml). The resulting 3-dioctyldithiocarbamoyl-1,2-propanediol (78.2 grams) was then reacted with boric acid (6.2 grams) by the same procedure described in Example II.

An amber viscous liquid of the title compound (88.25 grams) was obtained in quantitative yield. The structure was confirmed by C-13 NMR and IR spectra.

Example V

Preparation of Borate Ester of 2-Bis(2-ethylhexyl) dithiocarbamoylethanol

The procedure of Method B of Example I was followed, except that 2-chloroethanol (4.03 grams) was allowed to react with $CS_2$ (3.3 ml) and bis(2-ethylhexyl)amine (12.7 grams).

The resulting 2-bis(2-ethylhexyl)dithiocarbamoyl ethanol (18.29 grams; 95% yield) was then reacted with boric acid (0.98 grams) by the same procedure as described in Example II to give the title compound as a yellowish viscous liquid.

Example VI

Preparation of Borate Ester of 3-Oleyldithiocarbamoyl-1,2-propanediol.

The 3-oleyldithiocarbamoyl-1,2-propanediol was prepared in a manner similar to that of Method B of Example I, except that the addition of $CS_2$ onto the amine was reversed, and the reaction was carried out below 10° C. to reduce the formation of undesired corresponding isothiocyanate. Thus, $CS_2$ (6.0 ml) was reacted with oleylamine (33.44 grams; 80% pure) in hexane (25 ml), followed by the addition of aqueous NaOH (4.0 grams in 40 ml $H_2O$) and 3-chloro-1,2-propanediol (11.05 grams).

After an aqueous work up, the reaction product obtained was found to be contaminated with a small amount of N-oleylisothiocyanate which was easily separated from the desired diol by column chromatography and elution with 60% ethyl acetate in hexane.

The isolated grey waxy 3-oleyldithiocarbamoyl-1,2-propanediol (30.48 grams; 73% yield) was then borated with boric acid (2.26 grams) by the procedure described in Example II above to give the desired compound as a yellow viscous liquid.

Evaluation of Compounds of This Invention

Example VII

Anti-wear Properties of the Compounds

The anti-wear properties of the compounds of the invention were preliminarily evaluated by the ASTM D-4172 four-ball wear test. The additives were added to a formulated 10W-30 oil A which contains no ZDDP. The formulation and elemental analysis of the various compositions are listed in Tables 1 and 2 below.

TABLE 1

Formulation of Experimental Oils

| Component | Formulated Oil A | Formulated Oil B | Formulated Oil C |
|---|---|---|---|
| 100 N Base Stock | 54.62 Wt % | 54.62 Wt % | 54.62 Wt % |
| 325 N Base Stock | 25.70 | 25.70 | 25.70 |
| Pour Point Depressant | 0.21 | 0.21 | 0.21 |
| Viscosity Index Improver | 7.29 | 7.29 | 7.29 |
| Detergent Inhibitor Package A | 11.18 | 11.18 | 11.18 |
| Detergent Inhibitor Package B | 0 | 0 | 0 |
| Experimental II | 0 | 1.0 | 0 |
| Total | 99.0 Wt % | 100 Wt % | 100 Wt % |

*Detergent inhibitor packages A and B are provided by the Lubrizol Company. DI package B is a regular package which may contain anti-oxidant, detergent, dispersant, rust-inhibitor, anti-foaming and about 11 wt % of an anti-wear additive (ZDDP). The DI package A has the exact same components as package B, except it contains no ZDDP.

TABLE 2

Elemental Analysis of Blends

| Component | Formulated Oil A | Formulated Oil B | Formulated Oil C |
|---|---|---|---|
| Zinc | 0 ppm | 0 ppm | 1155 ppm |
| Phosphorus | 0 ppm | 0 ppm | 1007 ppm |
| Sulfur | 2124 ppm | 3417 ppm | 4043 ppm |
| Boron | 0 ppm | 130 ppm | 0 ppm |
| Calcium | 1809 ppm | 1800 ppm | 1706 ppm |
| Magnesium | 470 ppm | 400 ppm | 410 ppm |
| Copper | 0 ppm | 0 ppm | 0 ppm |
| Chlorine | 246 ppm | 223 ppm | 202 ppm |
| Nitrogen | No Analysis | 954 ng/ml | 653 ng/ml |

The results of the four-ball wear test are given in Table 3 below.

TABLE 3

ASTM D-4172 Four-Ball Wear Test
(40 Kg, 75° C., 1200 RPM, 60 Minutes)

| Additive | Wt % | Wear Scar (mm) |
|---|---|---|
| None (Formulated Oil A alone) | — | 0.83 |
| Experiment I | 1.0 | 0.52 |
| Experiment II | 1.0 | 0.40 |
| Experiment II | 0.5 | 0.38 |
| Experiment II | 0.3 | 0.39 |
| Experiment III | 1.0 | 0.40 |
| Experiment IV | 1.0 | 0.41 |
| Experiment V | 1.0 | 0.46 |
| Experiment VI | 1.0 | 0.47 |

The experiment oil B which was blended with 1 wt % of experiment II in formulated oil A was further evaluated in the ASTM III-D wear screener engine test. The result was compared with the reference 10W-30 SF oil, REO 400, as well as with the experimental oil C which was blended with a regular DI package (about 1.3 wt % of ZDDP was calculated on the basis of elemental analysis). The formulations and elemental analysis of experimental oils B and C are given in Table 1 and 2 above.

The engine test results are shown in Table 4 below.

TABLE 4

ASTM III-D Wear Screener Engine Test

| Cam Plus Lifter Wear* ($\times 10^{-4}$ inch) | Reference Oil REO 400 | Exp. Oil B (containing 1 Wt % of Exp. II) | Exp. Oil C (containing About 1.3 Wt % of ZDDP) |
|---|---|---|---|
| Maximum | 50.1 ± 16.2 | 54 | 57 |
| Average | 23.8 ± 11 | 16 (±11)** | 37 (±13)** |
| Minimum | 8.5 ± 4.5 | 7 | 18 |

*The maximum/minimum cam plus lifter wear was reported the highest/lowest wear of camshaft lobe plus valve lifter among the sixteen (16) pairs. The average cam plus lifter wear was reported by taking the average wear value of camshaft lobe plus valve lifter of sixteen (16) pairs.
**Standard deviations are shown in parenthesis.

The results demonstrate that the wear prevention performance of the experimental oil B, a 0% phosphorus oil containing the compound in the present invention, is superior to that of the experimental oil C, a conventional ZDDP-containing oil. The lower numbers show lower wear.

Example VIII

Anti-Friction Properties

The coefficients of friction were measured by the Optimol SVR Friction Coefficient test, a modified version of the SRV wear test, using a specimen piston ring to replace the standard ball on top of a cast iron disc.

The test was performed at a temperature of 100° C., a load of 200N, a frequency of 40 Hz and a duration of one hour. The coefficients of friction were reported at the end of the test.

Compounds representative of this invention were evaluated at 1 wt % concentration in the above prepared formulated 10W-30 oil A, and the results are given in Table 5 below.

TABLE 5

Coefficient of Friction

| Additive | Wt % | Coefficient of Friction |
|---|---|---|
| None (Formulated Oil A alone) | — | 0.152 |
| Experiment II | 1.0 | 0.141 |
| Experiment IV | 1.0 | 0.115 |
| Experiment VI | 1.0 | 0.114 |

This demonstrates that the compounds of the present invention improve the anti-friction properties of lubricating oils, especially when $R^1$ or $R^2$ in formula I contain a long, straight hydrocarbon chain.

Example IX

Anti-oxidant Properties

The anti-oxidant properties of compounds in this invention were evaluated by the well known Penn State micro-oxidation test.

A test oil film, exposed to air, is rested on a hot steel surface at 125° C. for 40 minutes. Any molecular weight change produced is monitored by gel permeation chromatography. The percentages of high molecular weight (% HMW) and the same molecular weight (% SMW) were measured after the tested oil was oxidized, the higher the percentage of high molecular weight, the poorer the oil oxidative stability of the oil.

The results of representative examples are given in Table 6 below.

TABLE 6

Mico-Oxidation Results
(Average of Two Runs)

| Additive | Wt % | % HMW | % SMW |
|---|---|---|---|
| None (Formulated Oil A alone) | — | 15.90 | 40.05 |
| Experiment II | 1.0 | 4.25 | 53.75 |
| Experiment IV | 1.0 | 4.10 | 52.71 |

Example X

Anti-Rust Properties

The rust-preventing characteristics of the compounds are determined by the ASTM D-665 test. In this test, a round steep specimen is fitted to a plastic holder and is rotated in a mixture of the test oil and distilled water at 140° F. for 24 hours.

The specimen is then rated "pass" or "fail". A "pass" rating requires that the specimen be rust-free at the end of a test period.

The evaluations were performed at 1 wt % of additives in 100N basestock oil. The results of the representative examples are shown in Table 7 below.

TABLE 7

ASTM D-665: Rust-Preventing Test

| Additive | Wt % | Result |
|---|---|---|
| None (100 N Base stock) | — | Fail (Severe Rust) |
| Example II | 1.0 | Pass |
| Example III | 1.0 | Pass |
| Example IV | 1.0 | Pass |

The invention now being fully described, it will be apparent to one of ordinary skill in the art that many changes and modifications can be made thereto without departing from the spirit or scope of the invention as set forth herein.

I claim:

1. An alkyldithiocarbamoyl alkanol of the formula

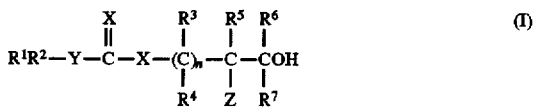

wherein

Z is OH or H;

Y is N,

X is S;

$R^1$ and $R^2$ are, independent of one another, selected from the group consisting of H, ($C_8$–$C_{40}$)hydrocarbon group and ($C_3$–$C_{50}$) cycloalkyl, aryl and aralkyl, but only one of $R^1$ and $R^2$ can be H;

$R^3$, $R^4$, $R^5$, $R^6$ and $R^7$ are, independent of one another, selected from the group consisting of H and ($C_1$–$C_8$) hydrocarbon group; and n is 0 to 4.

2. The alkyl dithiocarbamoyl alkanol of claim 1, wherein Z is OH and n is 0.

3. The alkyl dithiocarbamoyl alkanol of claim 1 being selected from the group consisting of 3-bis(2-ethylhexyl)dithiocarbamoyl-1,2-propanediol;

3-dioctyl dithiocarbamoyl-1,2-propanediol;

2-bis(2-ethylhexyl)dithiocarbamoyl ethanol; and 3-oleyl dithiocarbamoyl-1,2-propanediol.

4. The alkyl dithiocarbamoyl alkanol of claim 1, wherein $R^3$, $R^4$, $R^5$, $R^6$ and $R^7$ are ($C_1$–$C_8$) hydrocarbon group.

5. An alkyl dithiocarbamoyl alkanol of claim 1, which is 3-bis(2-ethylhexyl)dithiocarbamoyl-1,2-propanediol.

6. An alkyl dithiocarbamoyl alkanol of claim 1, which is 3-dioctyl dithiocarbamoyl-1,2 -propanediol.

7. An alkyl dithiocarbamoyl alkanol of claim 1, which is 2-bis(2-ethylhexyl)dithiocarbamoyl ethanol.

8. An alkyl dithiocarbamoyl alkanol of claim 1, which is 3-oleo dithiocarbamoyl-1,2-propanediol.

* * * * *